US012673021B2

(12) United States Patent
Dudler et al.

(10) Patent No.: US 12,673,021 B2
(45) Date of Patent: Jul. 7, 2026

(54) USE OF CAVIAR EXTRACTS

(71) Applicant: LA PRAIRIE GROUP AG, Volketswil (CH)

(72) Inventors: Bernhard Dudler, Hinwil (CH); Daniel Stangl, Meggen (CH)

(73) Assignee: LA PRAIRIE GROUP AG, Zürich (CH)

( * ) Notice: Subject to any disclaimer, the term of this patent is extended or adjusted under 35 U.S.C. 154(b) by 386 days.

(21) Appl. No.: 18/311,319

(22) Filed: May 3, 2023

(65) Prior Publication Data

US 2023/0355507 A1 Nov. 9, 2023

(30) Foreign Application Priority Data

May 4, 2022 (EP) .................................... 22171530

(51) Int. Cl.
*A61K 8/98* (2006.01)
*A61Q 19/08* (2006.01)

(52) U.S. Cl.
CPC .............. *A61K 8/987* (2013.01); *A61Q 19/08* (2013.01)

(58) Field of Classification Search
CPC ................................ A61K 8/987; A61Q 19/08
See application file for complete search history.

(56) References Cited

U.S. PATENT DOCUMENTS

2007/0087405 A1 4/2007 Chou et al.
2014/0037752 A1* 2/2014 Gammelsaeter ....... A61K 8/982 424/582
2015/0374603 A1* 12/2015 Wu ...................... A61K 9/0014 514/275
2020/0188447 A1* 6/2020 Stangl .................. A61K 31/425
2022/0160607 A1 5/2022 Auriol et al.

FOREIGN PATENT DOCUMENTS

CN 112791040 A 5/2021
KR 20030075297 A 9/2003
KR 20160036119 A 4/2016
WO WO-2018215219 A1 * 11/2018 .............. A61P 17/00
WO 2020201185 A1 10/2020

OTHER PUBLICATIONS

Google translation of KR20030075297A pp. 1-11 (Sep. 2003) (Year: 2003).*
Meunier et al "Mannose-6-phosphate complex and improvement in biomechanical properties of the skin" J. of Cosmetic Dermatology (2021) vol. 20 p. 1598-1610.*
Kudenziev et al., "Supercritical fluid extraction of fish oil from common carp (*Cypronus carpio*L.) tissues", The Journal of Supercritical Fluids, vol. 133, Dec. 1, 2017, pp. 528-534.

* cited by examiner

*Primary Examiner* — Bethany P Barham

(74) *Attorney, Agent, or Firm* — Abel Schillinger, LLP

(57) ABSTRACT

A method for the expression and/or for the amplification of the expression of thrombospondin-1, fibronectin, vimentin and/or mimecan in human skin. the method comprises applying to human skin at least one caviar extract which is capable of causing the expression and/or the amplification of the expression of thrombospondin-1, fibronectin, vimentin and/or mimecan in human skin.

20 Claims, No Drawings

USE OF CAVIAR EXTRACTS

CROSS-REFERENCE TO RELATED APPLICATIONS

The present application claims priority under 35 U.S.C. § 119 of European Patent Application 22171530.3, filed May 4, 2022, the entire disclosure of which is expressly incorporated by reference herein.

BACKGROUND OF THE INVENTION

1. Field of the Invention

The present invention relates to the cosmetic use of caviar extracts.

2. Discussion of Background Information

A known nuisance for many women and men is that the skin, in particular the skin of the face, loses volume and firmness with increasing age. As a consequence, in some circumstances, the contours of the face may visibly change. One result is the undesired formation of wrinkles.

The market offers a large number of cosmetic active ingredients and preparations which on repeated daily application to the skin lead to a reduction in the depth of wrinkles. However, a fundamental understanding of the skin structure is crucial for the effective treatment of wrinkles.

Tissues consist primarily of two different elements: living cells and the extracellular matrix. The extracellular matrix (ECM) functions as a kind of filler material lying between the otherwise densely packed cells. The ECM known as connective tissue can also serve to connect tissues such as the skin and muscles.

The ECM is a complex structure consisting of various proteins, proteoglycans and polysaccharides that provides a framework for cells, retains water and modulates biological processes such as cell adhesion, migration, repair, survival and development.

The role of the ECM in cell adhesion and signal transduction into the cells is performed by integrins, which transduce signals through the cell membrane in order to activate intracellular signal transduction. This crosstalk between the ECM and the cells regulates many cellular activities that are important for maintaining homeostasis of the tissue.

In the skin, the ECM forms a specific structure consisting of thick horizontal and vertical elements and a network-like fine structure in-between which structures the spatial distribution of the skin cells in the various layers (epidermis, dermis and hypodermis).

The retinacula cutis are connective tissue strands that pervade through the subcutis and anchor the skin to deeper-lying structures (periosteum, fasciae). They restrict the skin's movability. The retinacula cutis form a continuous network of fibrous extracellular matrix in the hypodermis. The fiber bundles consist of an aggregation of fibers that run more or less vertically from the outer layer of the deep fascia and form thin connections with the base of the dermis. Not all fibers extend over the full thickness of the hypodermis. Horizontal branches divide the hypodermis into two or three layers, also referred to as superficial fasciae. If blood vessels or nerves are present, the fibers of the skin ligaments form a fibrous sheath around these structures.

Between the fibers, a fine network of extracellular matrix elements serves to attach the cells of the adipose tissue, primarily adipocytes and preadipocytes, to the skin ligaments and acts as a framework that structures the spatial distribution of the cells.

Skin ligaments can be visualized in a very simplified manner as a tree, where the fibers represent the trunk and the thick branches of a tree and the fine network of ECM elements are all thin branches of a tree.

The fibers of the skin ligaments are primarily formed of collagen I and elastin, supplemented by proteoglycans such as mimecan (osteoglycin), decorin, prolargin, lumican and biglycan. The fibers are connected to the fine network of extracellular matrix elements, which serve to attach the cells of the adipose tissue to the skin ligaments.

Inter alia, fibronectin, laminin (associated with fibronectin and collagen IV), SPARC, thrombospondin, collagen IV, collagen V and collagen VI take part in this binding.

Fibronectin and collagen VI are essential for the anchorage of the collagen IV-coated adipocytes to the fibrous collagen structures.

Extracellular fibronectin and laminin form networks with collagen fibers and provide linkage points for integrins that are anchored in the adipocyte membrane. Fibronectin is an important ECM protein that in close association with type I collagen defines the cell shape and contractility of adipocytes.

Collagen IV is a primary component which covers the surface of adipocytes and is essential for the survival of the adipocytes.

Vimentin is an intracellular protein of the cytoskeleton, which is not part of the ECM. It makes an essential contribution to the mechanical strength of the subcutis. It covers, in a cage-like structure, the oil droplet(s) within adipocytes. The vimentin cage stabilizes the oil droplets like an exoskeleton, provides mechanical resistance and supports the cushioning effect of the subcutis.

Thrombospondin-1 is an adhesive protein which mediates cell-to-cell and cell-to-ECM interactions. In adipose tissue, it supports the anchorage of adipocytes to the skin ligaments. Consequently, it serves for the anchorage of constituents of the skin. An increased expression thus promotes the skin condition through improved anchorage of adipocytes to the skin ligaments.

As can be gathered from the statements, the structure of human skin is composed of complex relationships. However, the density and strength of the skin ligaments (retinacula cutis) decreases with age. It has been found that the concentrations of key components, such as thrombospondin-1, fibronectin, vimentin and mimecan, have an influence on the skin condition. The expression of these components can decrease with increasing age. This can in turn lead to the appearance of ageing phenomena such as sagging, wrinkles and losses of firmness and probably also of volume.

Accordingly, the literature contains a large number of attempts to amplify the expression of components of the skin structure. U.S. Pat. No. 7,279,329 B2 describes the promotion of collagen I.

However, the known attempts must not distract from the fact that there remains a need for particularly effective active ingredients and ingredient combinations that improve the expression of thrombospondin-1, fibronectin, vimentin and mimecan and thus reduce the appearance of ageing phenomena such as sagging, wrinkles and loss of firmness and volume.

Surprisingly, it has now been found that specifically the expression of thrombospondin-1, fibronectin, vimentin and mimecan can be increased through the use of caviar extracts.

SUMMARY OF THE INVENTION

The present invention provides for the use of at least one caviar extract for the expression of thrombospondin-1, fibronectin, vimentin and/or mimecan.

The present invention also provides for the use of a cosmetic preparation containing at least one caviar extract for the expression of thrombospondin-1, fibronectin, vimentin and/or mimecan.

The present invention also provides for the use of at least one caviar extract for the amplification of the expression of thrombospondin-1, fibronectin, vimentin and/or mimecan.

The present invention also provides for the use of a cosmetic preparation comprising at least one caviar extract for the amplification of the expression of thrombospondin-1, fibronectin, vimentin and/or mimecan.

The invention further provides for the use of at least one caviar extract for reinforcing the skin ligaments or the retinacula cutis and/or the connective tissue strands in human skin. Reinforcement in this context means that the connective tissue strands become less tight and thus wearing out of the tissue is prevented.

It is particularly advantageous for the invention when a cosmetic use is involved.

Advantageously, the use is effected by application of the components to human skin. A medical use is advantageously excluded.

The skin ligaments are also referred to as retinaculum cutis. The retinacula cutis are connective tissue strands that pervade through the subcutis and anchor the skin (cutis) to deeper-lying structures (periosteum, fasciae). They restrict the skin's movability.

The amplified expression of the mentioned components brings about a direct reinforcement of the skin ligaments, so that there is a reduction in skin ageing phenomena, such as sagging, wrinkles and loss of firmness and volume.

It is particularly surprising that the invention intensively promotes the expression of thrombospondin-1. Thrombospondin-1 is an adhesive protein which mediates cell-to-cell and cell-to-ECM interactions. In adipose tissue, it supports the anchorage of adipocytes to the skin ligaments. Consequently, it serves for the anchorage of constituents of the skin. An increased expression thus promotes the skin condition through improved anchorage of adipocytes to the skin ligaments.

All percentages by weight (% by weight) listed hereinafter are based, unless specified otherwise, in each case on the total weight of the cosmetic preparation. Where reference is made hereinafter to ratios, these refer, unless specified otherwise, to ratios by weight.

Unless specified otherwise, all experiments and process steps were conducted under normal conditions. The term "normal conditions" means 20° C., 1013 hPa and a relative humidity of 50%.

In the context of the present disclosure, the formulations "according to the invention", "advantageous according to the invention", "advantageous for the purposes of the present invention" etc. always relate to the use according to the invention.

Where the term skin is used hereinafter, this refers exclusively to human skin.

"Glycols" refers to those dialcohols (dihydric alcohols) that are derived from ethylene glycol (what are known as 1,2-diols or vicinal diols). Examples of these are ethylene glycol and propylene glycol.

The invention comprises at least one caviar extract. Caviar extracts are declared in cosmetic products under the INCI name "Caviar Extract".

Advantageously, the total content of caviar extract in the cosmetic preparations used according to the invention is from 0.1% to 5% by weight, preferably from 0.2% to 4% by weight and particularly preferably from 0.5% to 3.5% by weight, based on the total weight of the respective preparation.

Caviar extracts are generally commercially available under various trade names. An example is Creanatural® Caviar Sevruga Extract, produced by The Innovation Company. Further caviar extracts can be commercially obtained from the Mibelle Biochemistry Group.

According to the invention, "caviar extract" is to be understood as meaning extracts of sturgeon fish eggs. Known, inter alia, are the Siberian sturgeon, the shortnose sturgeon, the Yangtze sturgeon, the lake sturgeon, the Russian sturgeon, the green sturgeon, the Sakhalin sturgeon, the Adriatic sturgeon, the ship sturgeon, Acipenser oxyrinchus, the Persian sturgeon, the sterlet, the Japanese sturgeon, the Chinese sturgeon, the starry sturgeon, the European sea sturgeon, the white sturgeon, the kaluga, and the beluga, which is often referred to as the beluga sturgeon. It should be noted here that a large number of sturgeon species are threatened with extinction, meaning that the use thereof should be avoided. Most preferably according to the invention, the fish eggs of the white sturgeon (Acipenser transmontanus) and/or of the Siberian sturgeon (Acipenser baerii) are chosen. The white sturgeon is classed as not threatened according to the IUCN (International Union for Conservation of Nature and Natural Resources).

It is particularly advantageous when exclusively fish eggs of farmed sturgeon, in particular of farmed Siberian and/or white sturgeon, are used to prepare the caviar extract. It is furthermore extremely preferable when the fish eggs are obtained by a method which is not lethal to the fish.

In general, the caviar extracts according to the invention are advantageously prepared by a process comprising (1) homogenizing the provided fish eggs in at least one solvent, (2) extracting at least one liquid phase from the homogenizate obtained in (1), and (3) optionally filtering the extract obtained in (2) in order to remove solid suspended materials from the extract.

Further purification steps are possible in general.

It is advantageous according to the invention when at least one caviar extract is used which has the particular feature that in the preparation thereof at least water, but no glycol, or glycol in proportions by weight of water to glycol of from 1.1:1.0 to 1000:1.0, is added as solvent during the homogenization of the fish eggs and in which the aqueous phase is extracted to obtain the caviar extract. This extract is referred to as hydrophilic caviar extract. It is particularly surprisingly well suited to increasing/amplifying or else stimulating the expression of mimecan and/or fibronectin.

It is advantageous according to the invention when at least one caviar extract has the particular feature that in the preparation thereof at least glycol and optionally water are added as solvent during the homogenization of the fish eggs, where the proportions by weight of water to glycol are from 1.0:1.0 to 1.0:1000, and in which the glycolic phase is extracted to obtain the caviar extract. The glycolic phase is the phase that contains glycol. This extract is referred to as glycolic caviar extract. It is particularly surprisingly well suited to increasing/amplifying or else stimulating the expression of mimecan, vimentin and/or fibronectin.

It is furthermore advantageous according to the invention when at least one caviar extract is used, in the preparation of which at least oil is added as solvent during the homogenization of the fish eggs and in which the oil phase is extracted. Accordingly, an oil phase is obtained that features the caviar extract. Advantageously here, as oils, triglycerides are used, with particular preference being given to caprylic/capric triglyceride. This extract is referred to as lipophilic caviar extract. It is particularly surprisingly well suited for increasing/amplifying or else stimulating the expression of thrombospondin, especially thrombospondin-1, and/or fibronectin.

It is particularly advantageous to use at least two different caviar extracts, wherein a first lipophilic caviar extract is used, in the preparation of which at least oil, advantageously caprylic/capric triglyceride, is added as solvent during the homogenization of the fish eggs and in which the oil phase is extracted to obtain the extract, and wherein a second hydrophilic or glycolic caviar extract is used, in the preparation of which at least water and/or a glycol are added as solvent during the homogenization of the fish eggs and in which the aqueous and/or the glycolic phase is extracted to obtain the second extract.

It is furthermore particularly advantageous when three different caviar extracts are used, where a first lipophilic caviar extract as defined above, a second aqueous caviar extract as defined above, and a third glycolic caviar extract as defined above are used. As a result of the combination, surprisingly advantageous results in relation to the invention could be achieved.

As regards the lipophilic caviar extract, it is preferable when, in addition to the oil, which is advantageously caprylic/capric triglyceride, water is added during the homogenization. In this case, there is a separation of the lipophilic and hydrophilic constituents of the homogenizate. Correspondingly, predominantly lipophilic constituents of the homogenizate are extracted during the extraction of the oil phase. In this process it is advantageous when the added oils for homogenization contain at least caprylic/capric triglyceride, and furthermore advantageously the proportion of caprylic/capric triglyceride is at least 90% by weight based on the total weight of all added oils. It is furthermore advantageous when the proportion by weight of the fish eggs to the added oil phase during the homogenization is from 1.0:0.1 to 1.0:1.0 and in particular from 1.0:0.2 to 1.0:0.5.

If water is added for the homogenization, the proportion by weight of the fish eggs to the aqueous phase formed by addition of water is from 1.0:10 to 1.0:1.0, preferably from 1.0:8.0 to 1.0:2.0 and particularly preferably from 1.0:5.0 to 1.0:3.0.

As regards the aqueous caviar extract, it is preferable when, in addition to the water, at least one oil, advantageously caprylic/capric triglyceride, is additionally added during the homogenization. In this case, there is a separation of the lipophilic and hydrophilic constituents of the homogenizate. Correspondingly, predominantly hydrophilic constituents of the homogenizate are extracted during the extraction of the water phase. In this process it is advantageous when the added oil for homogenization contains at least caprylic/capric triglyceride, and furthermore advantageously the proportion of caprylic/capric triglyceride is at least 90% by weight based on the total weight of all added oils. It is furthermore advantageous when the proportion by weight of the fish eggs to the added oil phase during the homogenization is from 1.0:0.1 to 1.0:1.0 and in particular from 1.0:0.2 to 1:0.5. The proportion of the fish eggs to the aqueous phase is advantageously from 1.0:10 to 1.0:1.0, preferably from 1.0:8.0 to 1.0:2.0 and particularly preferably from 1.0:5.0 to 1.0:3.0. It is advantageous per se when the aqueous caviar extract is free of glycols, or the proportions of glycol represent less than 10% by weight based on the total weight of the extract. Advantageously, no glycol is added during or for the homogenization and extraction.

As regards the glycolic caviar extract, it is preferable when propylene glycol is added during the homogenization. In addition to propylene glycol, it is furthermore advantageous when water is also added. The proportion of propylene glycol to water is advantageously from 20:1.0 to 1.0:1.0, preferably 12:1.0 to 2.0:1.0 and particularly preferably 10:1.0 to 5.0:1.0. In this case, constituents of the homogenizate, which are possibly insoluble in pure water, are dissolved in the glycolic solution. After the homogenization, the glycolic phase is extracted. It is furthermore advantageous when the proportion by weight of the fish eggs to the added glycol, in particular to propylene glycol, is from 1.0:0.1 to 1:100 and in particular from 1.0:0.2 to 1.0:20 and in particular 1.0:0.5 to 1.0:10.

The active ingredient composition possibly varies depending on the extraction process described.

Advantageously, in the above embodiment the ratio by weight of the lipophilic caviar extract to the aqueous caviar extract is from 50:1 to 1:10, preferably from 30:1 to 1:1 and particularly preferably from 15:1 to 5:1.

Advantageously, in the above embodiment the ratio by weight of the lipophilic caviar extract to the glycolic caviar extract is from 50:1 to 1:50, preferably from 20:1 to 1:20 and particularly preferably from 10:1 to 1:10.

In addition to caviar extract, it is advantageous when mannose phosphate and/or sodium mannose phosphate are additionally added to the cosmetic preparation.

It is particularly preferable when the sodium mannose phosphate present is sodium mannose 6-phosphate. This is commercially available under the name Sodium mannose 6-phosphate from Sigma Aldrich.

It is likewise preferable when the mannose phosphate present is mannose 6-phosphate.

Advantageously, the ratio by weight of the entirety of the caviar extracts according to the invention to mannose phosphate and/or sodium mannose phosphate is from 200:1 to 1:50, preferably from 100:1 to 1:10, more preferably from 50:1 to 1:1 and particularly preferably from 30:1 to 2:1.

Advantageously, the ratio by weight of the entirety of the caviar extracts according to the invention to mannose 6-phosphate and/or sodium mannose 6-phosphate is from 200:1 to 1:50, preferably 100:1 to 1:10, preferably from 50:1 to 1:1 and particularly preferably from 30:1 to 2:1.

It is additionally advantageous according to the invention when mannose is added to the preparation. Advantageously, the ratio by weight of the entirety of the caviar extracts according to the invention to mannose is from 200:1 to 1:50, preferably from 100:1 to 1:10, more preferably from 50:1 to 1:1 and particularly preferably from 30:1 to 2:1. It is furthermore advantageous when sodium mannose phosphate and/or mannose phosphate are used together with propane-1,2,3-triol. Accordingly, propane-1,2,3-triol is advantageously present.

The invention is advantageously used in a very wide range of cosmetic preparations. These are likewise used in accordance with the invention.

The cosmetic preparations according to the invention may be present in the customary cosmetic preparation presentation forms, preferably as gel, O/W emulsion, W/O emulsion, W/O/W emulsion, O/W/O emulsion, microemulsion and cosmetic stick.

The cosmetic preparations according to the invention may be present preferably as emulsion, ointment, foundation, toner, aqueous solution, cream, gel, powder, mask, foam preparation and aerosol preparation.

Cosmetic preparations which are applied to the facial skin for daily care are usually formulated as emulsions. Emulsions are generally understood to mean heterogeneous systems which consist of two liquids which are immiscible or miscible only to a limited extent, one of the two liquids being dispersed in the form of very fine droplets in the other liquid. With the naked eye, an emulsion appears homogeneous. If the two liquids are water and oil, and the oil is present as finely distributed droplets in the water, then this is an oil-in-water emulsion (O/W emulsion). On the other hand, if the water is present as finely distributed droplets in the oil, then this is a water-in-oil emulsion (W/O emulsion).

It is particularly advantageous according to the invention when the cosmetic preparation is in the form of an O/W emulsion.

Emulsifiers serve to stabilize emulsions. Stabilization in this context means that the phase separation of the emulsion is prevented or delayed. Accordingly, stable emulsions can be produced by using appropriately selected emulsifier systems.

Emulsifiers are molecules with a polar, hydrophilic structural element and a nonpolar, lipophilic structural element. In general, such molecules can be defined by the HLB value (dimensionless number between 0 and 20) which indicates whether a preferential water or oil solubility is present. Water-in-oil emulsifiers (W/O emulsifiers) usually have an HLB value in the range from 3 to 8. Accordingly, W/O emulsifiers promote the stabilization of an aqueous phase which is present suspended in an oil phase. Oil-in-water emulsifiers (O/W emulsifiers) have an HLB value of greater than 8 to 18. These promote the stabilization of an oil phase which is present suspended in an aqueous phase.

If the cosmetic preparation is present as an oil-in-water emulsion, it is advantageous if the cosmetic preparation contains at least one O/W emulsifier with an HLB value in the range from greater than 8 to 18. O/W emulsifiers to be advantageously selected can be found for example in the following list:

| HLB value | Chemical name |
|---|---|
| 8.2 | Triglycerol monooleate |
| 8.3 | Diethylene glycol monolaurate |
| 8.4 | Polyoxyethylene (4) cetyl ether |
| | Polyoxyethylene glycol (400) dioleate |
| 8.5 | Sodium caproyl lactylate |
| | Polyethylene glycol (200) monostearate |
| | Sorbitan monooleate |
| 8.6 | Sorbitan monolaurate |
| | Polyethylene glycol (200) monolaurate |
| 8.8 | Polyoxyethylene (4) myristyl ether |
| | Polyethylene glycol (400) dioleate |
| 8.9 | Nonylphenol, polyoxyethylated with 4 mol of EO |
| 9.0 | Oleth-5 |
| 9.2-9.7 | Polyoxyethylene (4) lauryl alcohol |
| 9.3 | Polyoxyethylene (4) tridecyl alcohol |
| 9.6 | Polyoxyethylene (4) sorbitan monostearate |
| 9.8 | Polyethylene glycol (200) monolaurate |
| 10-11 | Polyethylene glycol (400) monooleate |
| 10.0 | Didodecyldimethylammonium chloride |
| 10.0 | Polyethylene glycol (200) monolaurate |
| | Polyethylene glycol (400) dilaurate |
| | Polyethylene glycol (600) dioleate |
| | Polyoxyethylene (4) sorbitan monostearate |
| | Polyoxyethylene (5) sorbitan monooleate |
| 10-12 | Glyceryl Stearate Citrate |
| 10.2 | Polyoxyethylene (40) sorbitol hexaoleate |
| 10.4-10.6 | Polyoxyethylene glycol (600) distearate |
| 10.5 | Polyoxyethylene (20) sorbitan tristearate |
| 10.6 | Sucrose monostearate |
| 10.7 | Sucrose monooleate |
| 11-11.4 | Polyethylene glycol (400) monooleate |
| 11.0 | Polyethylene glycol (350) monostearate |
| | Polyethylene glycol (400) monotallate |
| | Polyoxyethylene glycol (7) monostearate |
| | Polyoxyethylene glycol (8) monooleate |
| | Polyoxyethylene (20) sorbitan trioleate |
| | Polyoxyethylene (6) tridecyl alcohol |
| 11.1 | Polyethylene glycol (400) monostearate |
| 11.2 | Polyoxyethylene (9) monostearate |
| | Sucrose monooleate |
| | Sucrose monostearate |
| 11.4 | Polyoxyethylene (50) sorbitol hexaoleate |
| | Sucrose monotallate |
| | Sucrose stearate palmitate |
| 11.6 | Polyoxyethylene glycol (400) monoricinoleate |
| 11.7 | Sucrose monomyristate |
| | Sucrose monopalmitate |
| 12.0 | PEG-10 Soy Sterol |
| | Triethanolamine oleate |
| 12.2-12.3 | Nonylphenol, ethoxylated with 8 mol of EO |
| 12.2 | Sucrose monomyristate |

-continued

| HLB value | Chemical name |
|---|---|
| 12.4 | Sucrose monolaurate |
| | Polyoxyethylene (10) oleyl alcohol, polyoxyethylene (10) oleyl ether |
| | Polyoxyethylene (10) stearyl alcohol, polyoxyethylene (10) stearyl ether |
| 12.5 | Polyoxyethylene (10) stearyl cetyl ether |
| 12.7 | Polyoxyethylene (8) tridecyl alcohol |
| 12.8 | Polyoxyethylene glycol (400) monolaurate |
| | Sucrose monococoate |
| 12.9 | Polyoxyethylene (10) cetyl ether |
| 13 | Glycerol monostearate, ethoxylated (20 mol of EO) |
| 13.0 | Eumulgin O 10 (polyoxyethylene (10) oleyl ether) |
| | Eumulgin 286 (Nonoxynol-10) |
| | Eumulgin B 1 (Ceteareth-12) |
| 13.0 | C12 fatty amines, ethoxylated (5 mol of EO) |
| 13.1 | Nonylphenol, ethoxylated (9.5 mol of EO) |
| 13.2 | Polyethylene glycol (600) monostearate |
| | Polyoxyethylene (16) tall oil |
| 13.3 | Polyoxyethylene (4) sorbitan monolaurate |
| 13.5 | Nonylphenol, ethoxylated (10.5 mol of EO) |
| | Polyethylene glycol (600) monooleate |
| 13.7 | Polyoxyethylene (10) tridecyl alcohol |
| | Polyethylene glycol (660) monotallate |
| | Polyethylene glycol (1500) monostearate |
| | Polyoxyethylene glycol (1500) dioleate |
| 13.9 | Polyethylene glycol (400) monococoate |
| | Polyoxyethylene (9) monolaurate |
| 14-16 | Castor oil, ethoxylated with 40 EO and hydrogenated |
| 14.0 | Polyoxyethylene (12) lauryl ether |
| | Polyoxyethylene (12) tridecyl alcohol |
| 14.2 | Polyoxyethylene (15) stearyl alcohol |
| 14.3 | Polyoxyethylene (15) stearyl cetyl ether |
| 14.4 | Mixture of C12-C15 fatty alcohols with 12 mol of EO |
| 14.5 | Polyoxyethylene (12) lauryl alcohol |
| 14.8 | Polyoxyethylene glycol (600) monolaurate |
| 14.9-15.2 | Sorbitan monostearate, ethoxylated with 20 EO |
| 15-15.9 | Sorbitan monooleate, ethoxylated with 20 EO |
| 15.0 | PEG-20 Glyceryl Stearate |
| | PEG-40 Castor Oil |
| | Decyl glucoside |
| | Dodecyl glucoside |
| | Dodecyltrimethylammonium chloride |
| | Nonylphenol, ethoxylated with 15 mol of EO |
| | Polyethylene glycol (1000) monostearate |
| | Polyoxyethylene (600) monooleate |
| 15-17 | Castor oil, ethoxylated with 60 EO and hydrogenated |
| 15.3 | C12 fatty amines, polyoxyethylated with 12 mol of EO |
| | Polyoxyethylene (20) oleyl alcohol, polyoxyethylene (20) oleyl ether |
| 15.4 | Polyoxyethylene (20) stearyl cetyl ether |
| 15.5 | Polyoxyethylene (20) stearyl alcohol |
| 15.6 | Polyoxyethylene glycol (1000) monostearate |
| | Polyoxyethylene (20) sorbitan monopalmitate |
| 15.7 | Polyoxyethylene (20) cetyl ether |
| 15.9 | Disodium triethanolamine distearyl heptaglycol ether sulfosuccinate |
| 16.0 | Nonylphenol ethoxylated with 20 mol of EO |
| | Polyoxyethylene (25) propylene glycol stearate |
| 16-16.8 | Polyoxyethylene (30) monostearate |
| 16.3-16.9 | Polyoxyethylene (40) monostearate |
| 16.5-16.7 | Polyoxyethylene (20) sorbitan monolaurate |
| 16.6 | Polyoxyethylene (20) sorbitol |
| 16.7 | C18 fatty amines, polyoxyethylated with 5 mol of EO |
| | Polyoxyethylene (23) lauryl alcohol |
| 17.0 | Ceteareth-30, e.g., Eumulgin B 3 |
| | Octyl glucoside (Triton CG 110) |
| | Polyoxyethylene (30) glyceryl monolaurate |
| 17.1 | Nonylphenol, ethoxylated with 30 mol of EO |
| 17.4 | Polyoxyethylene (40) stearyl alcohol |
| 18.8 | PEG-100 Stearate |
| | Steareth-100 |
| 19.1 | PEG-80 Sorbitan Laurate |

In the above list, the abbreviation EO stands for ethylene oxide and PEG stands for polyethylene glycol.

According to the invention, such an O/W emulsion may advantageously also contain W/O emulsifiers, where the ratio of the O/W emulsifiers to the W/O emulsifiers, taking into account the respective HLB values, should be selected such that an O/W emulsion is formed. A known mixture of O/W emulsifiers and W/O emulsifiers is the commercial product Arlacel 170 from Croda containing Glyceryl Stearate and PEG-100 Stearate, the ratio of the two substances being chosen such that an overall HLB of approximately 11 results.

The cosmetic preparation according to the invention advantageously additionally contains oils selected from the group of lecithins and fatty acid triglycerides, namely the triglycerol esters of saturated and/or unsaturated, branched and/or unbranched alkanecarboxylic acids with a chain length of 8 to 24, especially 12 to 18 carbon atoms. The fatty acid triglycerides may advantageously be selected from the group of synthetic, semisynthetic and natural oils, such as for example olive oil, sunflower oil, soybean oil, peanut oil, rapeseed oil, almond oil, palm oil, coconut oil, castor oil, wheat germ oil, grapeseed oil, safflower oil, evening primrose oil, macadamia nut oil and the like.

Furthermore, the cosmetic preparation according to the invention may advantageously contain oils which are selected from the group of branched and unbranched hydrocarbons and hydrocarbon waxes, especially petroleum jelly (petrolatum), liquid paraffin, squalane and squalene, polyolefins and hydrogenated polyisobutenes. Among the polyolefins, polydecenes are the preferred substances.

Furthermore, the cosmetic preparation according to the invention may advantageously contain fat and/or wax components from the group of plant waxes, animal waxes, mineral waxes and petrochemical waxes. Favorable according to the invention are candelilla wax, carnauba wax, Japan wax, esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), uropygial fat, ceresin, ozokerite (earth wax), paraffin waxes and microwaxes.

Further advantageous fat and/or wax components are chemically modified waxes and synthetic waxes, such as for example those available under the trade names Syncrowax HRC (glyceryl tribehenate), and Syncrowax AW 1 C (C18-36 fatty acid) from CRODA GmbH, and also montan ester waxes, Sasol waxes, hydrogenated jojoba waxes, synthetic or modified beeswaxes (e.g. dimethicone copolyol beeswax and/or C30-50 alkyl beeswax), polyalkylene waxes, polyethylene glycol waxes, but also chemically modified fats, such as for example hydrogenated plant oils (for example hydrogenated castor oil and/or hydrogenated coconut fatty glycerides), triglycerides, such as for example trihydroxystearin, fatty acids, fatty acid esters and glycol esters, such as for example C20-40 alkyl stearate, C20-40 alkyl hydroxystearoyl stearate and/or glycol montanate.

It may also be advantageous for the purposes of the present invention when the cosmetic preparation contains cyclic, branched and/or linear silicones. The group of the cyclic, branched and/or linear silicones are also referred to, in the context of the present disclosure, as "silicone oils". Linear silicone oils are described by the INCI name Dimethicone and have a structure according to the formula (I)

$$(SiR^1_3)-O-(SiR^2_2-O)_x-(SiR^1_3), \qquad (I)$$

while branched silicone oils can be described according to the formula (II)

(II)

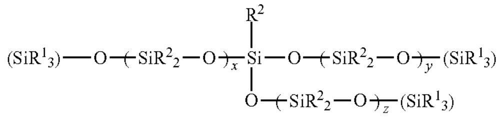

where $R^1$ and $R^2$ can independently be a hydrogen atom, a methyl group, or a linear or branched, saturated or unsaturated hydrocarbon group having 3 to 30 carbon atoms, and where x, y and z are independently integers in the range from 0 to 60 000. Cyclic silicones are known under the INCI name Cyclomethicone.

It is advantageous in this case if the proportion by weight of the silicone oils in the cosmetic preparation is from 3% by weight to 10% by weight, based on the total weight of the cosmetic preparation.

Furthermore, it is an advantageous particular feature of the cosmetic preparation that the total proportion of the oil phase in the O/W emulsion is from 2% to 30% by weight, preferably from 5% by weight to 25% by weight and particularly preferably from 8% by weight to 22% by weight, based on the total weight of the cosmetic preparation. The silicone oils also belong to the oil phase of the cosmetic preparation. Emulsifiers by definition do not belong to the oil phase of the cosmetic preparation according to the invention.

It is moreover advantageous when the total proportion of water in the cosmetic preparation according to the invention is from 50% by weight to 95% by weight, preferably from 60% by weight to 80% by weight, based on the total weight of the cosmetic preparation.

It is further advantageous when the cosmetic preparation contains one or more rheology modifiers. Rheology modifiers to be chosen with preference are selected from the group of the following INCI substances:

- Carbomer (Carbopols of the types 980, 981, 2984, 5984 from Lubrizol); Acrylates Copolymer (e.g. Carbopol® Aqua SF-1 polymer from Lubrizol), Acrylates/C10-30 Alkyl Acrylate Crosspolymer (e.g. Pemulen TR 1, Pemulen TR 2, Carbopol 1328 from Lubrizol), Hydroxyethyl Acrylates/Sodium Acryloyldimethyl Taurate Copolymer, Ammonium Acryloyldimethyltaurate/VP Copolymer (e.g. Aristoflex AVC from Clariant), Polyacrylate-1 Crosspolymer (e.g. Carbopol® Aqua CC polymer from Lubrizol); Sodium Polyacrylate (e.g. Cosmedia SP from BASF); copolymer of vinylpyrrolidone and acrylic acid
- Celluloses and cellulose derivatives, e.g. hydroxypropylmethylcellulose, methylcellulose, carboxymethylcellulose, hydroxyethylcellulose, hyaluronic acid and xanthan gum starches, for example tapioca starch.

Particular preference is given to selecting the rheology modifiers from the group of the substances known under the INCI names Carbomer, Acrylates/C10-30 Alkyl Acrylate Crosspolymer, Sodium Polyacrylate, Hydroxyethyl Acrylates/Sodium Acryloyldimethyl Taurate Copolymer and Ammonium Acryloyldimethyltaurate/VP Copolymer.

The total proportion of these rheology modifiers, in particular the total proportion of the rheology modifiers identified above as preferred, is advantageously from 0.05% to 5% by weight, preferably from 0.1% to 2.5% by weight, based on the total weight of the cosmetic preparation. Moreover, it is particularly advantageous when, in addition to the substances mentioned above as particularly preferred, tapioca starch is present in a proportion of up to 3.5% by weight, based on the total weight of the cosmetic preparation.

Furthermore, it is advantageous when the ratio by weight of all rheology modifiers according to the invention present to the oil phase present is from 1:1 to 1:30, preferably from 1:2 to 1:28, particularly preferably from 1:20 to 1:27. Such cosmetic preparations according to the invention have a surprisingly advantageous creaminess and are not perceived by the consumer as being crumbly or too oily and too liquid.

It is advantageous according to the invention when the cosmetic preparation according to the invention contains cetyl alcohol, stearyl alcohol or a mixture of cetyl alcohol and stearyl alcohol.

If the cosmetic preparation contains cetyl alcohol, stearyl alcohol or a mixture of cetyl alcohol and stearyl alcohol, it is advantageous according to the invention when the total proportion of these substances is from 0.5% to 5.5% by weight, based on the total weight of the cosmetic preparation.

It is moreover advantageous when the cosmetic preparation according to the invention additionally contains one or more substances selected from the group of ethanol, isopropanol, propylene glycol, propanediol, glycerol, ethylene glycol, ethylene glycol monoethyl or monobutyl ether, propylene glycol monomethyl, monoethyl or monobutyl ether and/or diethylene glycol monomethyl or monoethyl ether. It is preferable here when the cosmetic or dermatological preparation contains glycerol and/or propanediol.

It is likewise advantageous to use the cosmetic preparations according to the invention as sunscreens. Accordingly, the preparations for the purposes of the present invention preferably contain at least one UV-A, UV-B and/or broad-spectrum filter substance. The formulations may, although not necessarily, optionally also contain one or more organic and/or inorganic pigments as UV filter substances, where these may be present in the water phase and/or the oil phase.

The preparations according to the present invention may contain at least one room temperature-liquid UV filter substance.

Particularly advantageous room temperature-liquid UV filter substances for the purposes of the present invention are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Ethylhexyl Salicylate) and esters of cinnamic acid, preferably 4-methoxycinnamic acid 2-ethylhexyl ester (2-ethylhexyl 4-methoxycinnamate, INCI: Ethylhexyl Methoxycinnamate) and 4-methoxycinnamic acid isopentyl ester (isopentyl 4-methoxycinnamate, INCI: Isoamyl p-Methoxycinnamate), 3-(4-(2,2-bis(ethoxycarbonylvinyl)phenoxy)propenyl)methoxysiloxane/dimethylsiloxane copolymer, which is available for example under the trade name Parsol® SLX from Hoffmann La Roche.

Preferred inorganic pigments are metal oxides and/or other metal compounds that are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and blends of such oxides, and also barium sulfate ($BaSO_4$).

For the purposes of the present invention, the pigments may advantageously also be used in the form of commercially available oily or aqueous predispersions. Dispersing aids and/or solubilizers may be added to these predispersions.

The pigments may according to the invention advantageously be surface-treated ("coated"), where for example a hydrophilic, amphiphilic or hydrophobic character is to be formed or retained. This surface treatment may consist in providing the pigments with a thin hydrophilic and/or hydrophobic inorganic and/or organic layer by methods known per se. For the purposes of the present invention, the various surface coatings may also contain water.

Suitable titanium dioxide particles and predispersions of titanium dioxide particles are available under the following trade names from the companies listed:

| Trade name | Coating | Manufacturer |
| --- | --- | --- |
| MT-100TV | Aluminum hydroxide/stearic acid | Tayca Corporation |
| MT-100Z | Aluminum hydroxide/stearic acid | Tayca Corporation |
| Eusolex T-2000 | Alumina/simethicone | Merck KGaA |
| Titanium dioxide T805 (Uvinul $TiO_2$) | Octyltrimethylsilane | Degussa |
| Tioveil AQ 10PG | Alumina/Silica | Solaveil/Uniqema |
| Eusolex T-aqua | Water/alumina/sodium metaphosphate | Merck |

Advantageous UV-A filter substances for the purposes of the present invention are dibenzoylmethane derivatives, in particular 4-(tert-butyl)-4'-methoxydibenzoylmethane (CAS No 70356-09-1), which is sold by Givaudan under the brand Parsol® 1789 and by Merck under the trade name Eusolex® 9020.

Further advantageous UV filter substances for the purposes of the present invention are:

- phenylene-1,4-bis(2-benzimidazyl)-3,3'-5,5'-tetrasulfonic acid and salts thereof, especially the corresponding sodium, potassium or triethanolammonium salts, in particular phenylene-1,4-bis(2-benzimidazyl)-3,3'-5,5'-tetrasulfonic acid bis-sodium salt having the INCI name Disodium Phenyl Dibenzimidazole Tetrasulfonate (CAS No: 180898-37-7), which is available for example under the trade name Neo Heliopan AP from Symrise;
- salts of 2-phenylbenzimidazole-5-sulfonic acid, such as the sodium, potassium or triethanolammonium salt thereof and also the sulfonic acid itself having the INCI name Phenylbenzimidazole Sulfonic Acid (CAS No 27503-81-7), which is available for example under the trade name Eusolex 232 from Merck or as Neo Heliopan Hydro from Symrise;
- 1,4-di(2-oxo-10-sulfo-3-bornylidenemethyl)benzene (also: 3,3'-(1,4-phenylenedimethylene)bis(7,7-dimethyl-2-oxobicyclo[2.2.1]hept-1-ylmethanesulfonic acid) and salts thereof (especially the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephthalylidene Dicamphor Sulfonic Acid (CAS No: 90457-82-2) and is available for example under the trade name Mexoryl SX from Chimex;
- sulfonic acid derivatives of 3-benzylidenecamphor, such as for example 4-(2-oxo-3-bornylidenemethyl)benzenesulfonic acid, 2-methyl-5-(2-oxo-3-bornylidenemethyl)sulfonic acid and salts thereof.
- Benzoxazole derivatives, such as for example 2,4-bis[5-(1-dimethylpropyl)benzoxazol-2-yl(4-phenyl)imino]-6-(2-ethylhexyl)imino-1,3,5-triazine having the CAS No 288254-16-0, which is available from 3V Sigma under the trade name Uvasorb® K2A.
- Hydroxybenzophenones, for example hexyl 2-(4'-diethylamino-2'-hydroxybenzoyl)benzoate (also: aminobenzophenone), which is available under the trade name Uvinul A Plus from BASF.

Triazine derivatives, such as for example 2,4-bis{[4-(2-ethylhexyloxy)-2-hydroxy]phenyl}-6-(4-methoxyphenyl)-1,3,5-triazine (INCI: Bis-Ethylhexyloxylphenol Methoxyphenyl Triazine), which is available under the trade name Tinosorb® S from CIBA-Chemikalien GmbH; dioctylbutylamidotriazone (INCI: Diethylhexyl Butamido Triazone), which is available under the trade name UVASORB HEB from Sigma 3V; tris(2-ethylhexyl) 4,4',4"-(1,3,5-triazine-2,4,6-triyltriimino) tribenzoate, also: 2,4,6-tris[anilino(p-carbo-2'-ethyl-1'-hexyloxy)]-1,3,5-triazine (INCI: Ethylhexyl Triazone), which is sold by BASF Aktiengesellschaft under the trade name UVINUL® T 150; 2-[4,6-bis(2,4-dimethylphenyl)-1,3,5-triazin-2-yl]-5-(octyloxy)phenol (CAS No: 2725-22-6).

Benzotriazoles, such as for example 2,2'-methylenebis(6-(2H-benzotriazol-2-yl)-4-(1,1,3,3-tetramethylbutyl) phenol) (INCI: Methylene Bis-Benzotriazolyl Tetramethylbutylphenol), which is for example available under the trade name Tinosorb® M from CIBA-Chemikalien GmbH.

3-Benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

esters of benzalmalonic acid, preferably di(2-ethylhexyl) 4-methoxybenzalmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and polymer-bonded UV filters ethylhexyl 2-cyano-3,3-diphenylacrylate (Octocrylene), which is available from BASF under the name Uvinul® N 539 T.

Particularly advantageous cosmetic preparations for the purposes of the present invention, which feature a high or very high UV-A protection, preferably also contain, in addition to the filter substance(s) according to the invention, further UV-A and/or broad-spectrum filters, in particular dibenzoylmethane derivatives [for example 4-(tert-butyl)-4'-methoxydibenzoylmethane] and/or 2,4-bis{[4-(2-ethylhexyloxy)-2-hydroxy]phenyl}-6-(4-methoxyphenyl)-1,3,5-triazine and/or phenylene-1,4-bis(2-benzimidazyl)-3,3'-5,5'-tetrasulfonic acid bis-sodium salt, each individually or in any desired combinations with one another.

The list of said UV filters which can be used for the purposes of the present invention is of course not intended to be limiting.

The total amount of the filter substances is chosen from the range of from 0.1% to 30% by weight, preferably from 0.5% to 10% by weight, in particular from 1.0% to 8.0% by weight-based in each case on the total weight of the cosmetic preparations—in order to provide cosmetic or dermatological preparations which protect the hair or the skin from the entire range of ultraviolet radiation.

It is further advantageous when the cosmetic preparation according to the invention contains at least one further active ingredient for the cosmetic treatment and/or cosmetic prophylaxis of undesired skin pigmentation.

The cosmetic preparations may accordingly also contain further cosmetic adjuvants such as are conventionally used in such preparations, for example further consistency regulators, film formers, stabilizers, fillers, preservatives, fragrances, substances for preventing foaming, dyes, further pigments which have a coloring effect, surface-active substances, softening, moistening and/or moisturizing substances, anti-inflammatory substances, additional active ingredients such as vitamins or proteins, insect repellents, bactericides, virucides, salts, antimicrobial, proteolytic or keratolytic substances or other conventional constituents of a cosmetic formulation such as further alcohols, polyols, foam stabilizers, organic solvents or electrolytes.

To sum up, the present invention provides in particular:

1. A method for the expression and/or for the amplification of the expression of thrombospondin-1, fibronectin, vimentin and/or mimecan in skin, wherein the method comprises applying to skin at least one caviar extract which is capable of causing the expression and/or the amplification of the expression of thrombospondin-1, fibronectin, vimentin and/or mimecan in skin.
2. The method of item 1, wherein a cosmetic preparation comprising the at least one caviar extract is applied to the skin.
3. The method of item 1 or item 2, wherein the skin is human skin.
4. The method of any one of the preceding items, wherein thrombospondin-1, fibronectin, vimentin and/or mimecan are caused to be expressed in human skin.
5. The method of any one of the preceding items, wherein the at least one caviar extract has been obtained from fish eggs of white sturgeon (Acipenser transmontanus) and/or of Siberian sturgeon (Acipenser baerii).
6. The method of any one of the preceding items, wherein the at least one caviar extract has been obtained by a process comprising
   (1) homogenizing provided fish eggs in at least one solvent,
   (2) extracting at least one liquid phase from the homogenizate obtained in (1), and
   (3) optionally filtering the extract obtained in (2).
7. The method of any one of the preceding items, wherein at least one caviar extract is used, in a preparation of which at least water, but no glycol, or glycol in proportions by weight of water to glycol of from 1.1:1.0 to 1000:1.0, is added as solvent during the homogenization of the fish eggs and in which the aqueous phase of the homogenizate is extracted to obtain the caviar extract.
8. The method of any one of the preceding items, wherein at least one caviar extract is used, in the preparation of which at least glycol and optionally water are added as solvent during the homogenization of the fish eggs, where the ratio by weight of water to glycol is from 1.0:1.0 to 1.0:1000, and in which the glycolic phase of the homogenizate is extracted to obtain the caviar extract.
9. The method of any one of the preceding items, wherein at least one caviar extract is used, in the preparation of which at least oil is added as solvent during the homogenization of the fish eggs and in which the oil phase is extracted.
10. The method of item 9, wherein, as oil, triglycerides are used, with particular preference being given to caprylic/capric triglyceride.
11. The method of item 9 or item 10, wherein the ratio by weight of the fish eggs to the added oil phase during the homogenization is from 1.0:0.1 to 1.0:1.0 and in particular from 1.0:0.2 to 1.0:0.5.

12. The method of any one of items 7 to 11, wherein the ratio by weight of the fish eggs to the aqueous phase, when present, is from 1.0:10 to 1.0:1.0, preferably from 1.0:8.0 to 1.0:2.0 and particularly preferably from 1.0:5.0 to 1.0:3.0.
13. The method of any one of the preceding items, wherein mannose phosphate and/or sodium mannose phosphate are additionally employed.
14. The method of any one of the preceding items, wherein mannose is additionally employed.
15. A method of reinforcing the skin ligaments and/or the retinacula cutis and/or the connective tissue strands in human skin, wherein the method comprises applying at least one caviar extract which is capable of reinforcing the skin ligaments and/or the retinacula cutis and/or the connective tissue strands in human skin to human skin.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those of skill in the art how the several forms of the present invention may be embodied in practice.

Comparative Experiments and Examples

Unless otherwise indicated, all amounts, proportions and percentages are based on the weight and the total amount or on the total weight of the preparations.

The efficacy of the invention was verified in an ELISA test. ELISA (enzyme-linked immunosorbent assay) is a widespread method for detecting individual proteins. It utilizes the mechanisms of the immune system: If a substance is recognized as foreign by the immune system, the latter forms "antibodies" that bind to the foreign molecule and thus tag it.

To perform the experiments, hypodermis (from mammoplasty operations) from a healthy donor (56 years of age) was used. The hypodermis was prepared and weighed out into approximately 200 mg pieces. The tissue was cultured in a submersed state in defined and serum-free hypodermis tissue culture medium (CB-EM-HYP) in an actively humidified biomedical incubator (Memmert, Germany) at 37° C. and 5% CO2.

Overnight cultivation was followed by substitution with fresh tissue culture medium. Explants were cultivated either in the presence or absence of test samples.

Over a period of 10 days, the medium was replaced daily with freshly supplemented test samples or with normal media without test samples.

After 10 days of treatment, a portion of the tissue samples was processed for the extraction of ECM proteins.

Isolated ECM was subjected to a protein estimation in accordance with the BCA method (Bicinchoninic Acid) (Sigma Aldrich), and ELISAs (Biotechne) corresponding to the antigen to mimecan, fibronectin, thrombospondin-1 and vimentin were performed according to the manufacturer's protocol using the same amounts of proteins as were estimated from the BCA assay. A sensitive filter-based microplate reader (Accuris, USA) was used to perform readout. The ELISA results (% difference) were presented as percentage compared to the untreated control with mean value+/−SEM with repetitions in triplicate execution/condition.

The following test samples were investigated:

A. Glycolic caviar extract containing approx. 6% fish egg material, 10% water and propylene glycol ad 100. This extract was obtained from an extraction with propylene glycol of a homogenizate from fish eggs of Acipenser baerii. This extract is available commercially under the trade name Caviar B Glycolysat CH from Mibelle Biochemistry Group.

B. Aqueous caviar extract comprising approx. 21% fish egg material, 1% phenoxyethanol, 5% glycerol, 1% glycine, 0.5% xanthan gum, 0.2% galactaric acid and water ad 100. This extract was obtained from an extraction with water, glycine, xanthan gum and phenoxyethanol and galactaric acid of a homogenizate from fish eggs of Acipenser baerii. This extract is available commercially under the trade name Caviar B HydroEssence CH from Mibelle Biochemistry Group.

C. Lipophilic caviar extract containing 40% fish egg material, 0.02% tocopherol, 1% by weight phenoxyethanol and triglycerides ad 100. This extract was obtained from an extraction with triglycerides and phenoxyethanol of a homogenizate from fish eggs of Acipenser baerii. This extract is available commercially under the trade name Caviar B LipoEssence CH from Mibelle Biochemistry Group.

D. Mixture of glycerol, water, sodium mannose 6-phosphate and mannose. Agefinity commercial product from Givaudan. The proportion of sodium mannose 6-phosphate is 2.5% by weight. The proportion of mannose is 2.5% by weight.

The following table specifies the use concentrations of the extracts which were used in the comparative experiment against an untreated control.

| Test sample | Expression of mimecan in % relative to the control (100%) |
|---|---|
| Control (without addition) | 100% |
| 0.5% A | 153% |
| 0.5% B | 180% |

| Test sample | Expression of fibronectin in % relative to the control (100%) |
|---|---|
| Control (without addition) | 100% |
| 0.5% A | 118% |
| 0.5% B | 126% |
| 0.05% C | 118% |

| Test sample | Expression of vimentin in % relative to the control (100%) |
|---|---|
| Control (without addition) | 100% |
| 0.5% A | 156% |

| Test sample | Expression of thrombospondin-1 in % relative to the control (100%) |
|---|---|
| Control (without addition) | 100% |
| 0.05% C | 199% |
| 1% D | 118% |
| 1% mixture of A, B, C and D (ratios by weight of A/B/C/D: 1/0.1/1/4) | 360% |

The measurements performed clearly show that the expression of mimecan, fibronectin, vimentin and thrombospondin-1 could surprisingly be increased through the use of caviar extracts. In combination with mannose and sodium mannose 6-phosphate, synergy was even detected.

All measurement results shown are significantly ($p<0.05$) different compared to the untreated condition.

Further cosmetic exemplary formulations are listed hereinafter.

Exemplary Formulations:

| Example number | 1 | 2 | 3 | 4 | 5 |
|---|---|---|---|---|---|
| PEG-100 Stearate | 2.0 | 0.9 | | | |
| PEG-20 Glyceryl Stearate | | 1.1 | | | |
| PEG-40 Stearate | | | | | 1.0 |
| Ceteareth-25 | | | 0.5 | | |
| Steareth-100 | | | 0.5 | 2.0 | |
| Ceteth-20 | | | 1.0 | | |
| Myristyl Myristate | 1.0 | | | | 1.0 |
| Glyceryl Stearate | | 1.1 | | | 2.0 |
| Stearyl Alcohol | 2.0 | 1.0 | | | |
| Cetearyl Alcohol | | | | 4.0 | 2.5 |
| Cetyl Alcohol | 1.0 | | 3.0 | | |
| Hydrogenated Coco Glycerides | 2.0 | | | | |
| Butyrospermum Parkii (Shea) Butter | | 2.0 | | | 2.0 |
| C12-15 Alkyl Benzoate | | 3.0 | 2.0 | | 3.5 |
| Butylene Glycol Dicaprylate/Dicaprate | 1.0 | | | 1.5 | |
| Caprylic/Capric Triglyceride | | 1.0 | 1.0 | 2.0 | 2.0 |
| Ethylhexyl Cocoate | 3.0 | | | | 1.5 |
| Octyldodecanol | | | 1.0 | | |
| Paraffinum Liquidum | | 1.0 | | | |
| Cera Microcristallina | 2.0 | | 1.0 | | 1.5 |
| Cyclomethicone | 4.1 | 1.0 | 4.0 | 3.5 | 5.0 |
| Dimethicone | | 2.3 | 1.0 | 1.2 | |
| Dicaprylyl Ether | 1.0 | 4.0 | 2.0 | | |
| Dicaprylyl Carbonate | | | | 2.8 | |
| Ethylhexyl Methoxycinnamate | 4.0 | 3.0 | 5.0 | 2.0 | 2.5 |
| Disodium Phenyl Dibenzimidazole Tetrasulfonate | 1.0 | 1.0 | 1.5 | 0.5 | 2.0 |
| Phenylbenzimidazole Sulphonic Acid | 2.0 | 3.0 | 1.0 | 1.5 | 1.5 |
| Ethylhexyl Triazone | | | | | 2.0 |
| Octocrylene | | | | 2.5 | |
| Ethylhexyl Salicylate | | | 1.0 | | |
| Extract A | 0.1 | 0.2 | | | 0.5 |
| Extract B | | | 0.1 | | |
| Extract C | | | | 1 | |
| Biotin | | | | | 0.04 |
| Retinyl Palmitate | | | | 0.1 | |
| Thioctic Acid | 0.1 | | | | |
| Tocopheryl Acetate | | | 1.0 | | |
| Sodium Citrate | | 0.1 | | | |
| Sodium Ascorbyl Phosphate | 0.1 | | | | 0.1 |
| Trisodium EDTA | | 0.1 | | | |
| Phenoxyethanol | 0.4 | | 0.4 | 0.4 | 0.4 |
| Butylparaben | 0.6 | 0.3 | 0.2 | 0.3 | 0.3 |
| Alcohol Denat. | | 2.0 | | | |
| Xanthan Gum | 0.1 | | | | |
| Carbomer | 0.05 | | 0.1 | | 0.1 |
| Polyacrylamide | | 0.2 | | | |
| Glycerin | 10 | 6.0 | 6.5 | 7.5 | 8.0 |
| Butylene Glycol | 2.0 | 1.0 | | | |
| Fillers/additives (distarch phosphate, $SiO_2$, BHT, talc, aluminum stearate) | 0.1 | 1.0 | 0.2 | 0.5 | 0.05 |
| Parfum | q.s. | q.s. | q.s. | q.s. | q.s. |
| Aqua | ad 100 | ad 100 | ad 100 | ad 100 | ad 100 |

| Example number | 6 | 7 | 8 | 9 | 10 |
|---|---|---|---|---|---|
| PEG-50 Stearate | 2.5 | | | | 1.0 |
| PEG-40 Stearate | 1.0 | 1.0 | | | 0.5 |
| PEG-8 Stearate | | | | 1.0 | |
| PEG-8 Distearate | | | | | 1.0 |
| Glyceryl Stearate | | 3.0 | | | |
| Sorbitan Stearate | | 1.0 | | | |
| Steareth-21 | | | 2.0 | 1.0 | |
| Steareth-2 | | | 1.0 | | |

-continued

| | | | | | |
|---|---|---|---|---|---|
| Cetearyl Glucoside | | | | 2.0 | |
| Myristyl Myristate | | | | 1.0 | |
| Behenyl Alcohol | | 1.0 | | | 2.0 |
| Stearyl Alcohol | | | | 5.0 | |
| Cetearyl Alcohol | 3.0 | | 2.0 | | 1.0 |
| Cetyl Alcohol | | 1.0 | | | |
| Hydrogenated Coco Glycerides | 1.0 | | | | 1 |
| *Butyrospermum Parkii* (Shea) Butter | 2.5 | | | | |
| C12-15 Alkyl Benzoate | | 2.0 | 5.0 | 2.5 | |
| Butylene Glycol Dicaprylate/Dicaprate | 1.5 | | | | 2.0 |
| Caprylic/Capric Triglyceride | 1.0 | 1.5 | | 3.5 | |
| Ethylhexyl Cocoate | | | | | 2.0 |
| Octyldodecanol | | | 1.0 | | 1.5 |
| Paraffinum Liquidum | | | 1.0 | | |
| Cera Microcristallina | 1.8 | | | | |
| Cyclomethicone | 4.0 | 3.5 | 2.0 | 5.0 | 2.0 |
| Dimethicone | | | 2.0 | | 1.5 |
| Dicaprylyl Ether | | | 2.0 | | |
| Dicaprylyl Carbonate | | 2.0 | | 3.0 | 3.5 |
| N-(4-(2,4-Dihydroxyphenyl)thiazol-2-yl)isobutyramide | 0.1 | 0.15 | 0.25 | 0.1 | 0.5 |
| Polydecene | | | | 4 | |
| Ethylhexyl Methoxycinnamate | 2.0 | 3.0 | 4.5 | 5.0 | 4.2 |
| Phenylbenzimidazole Sulphonic Acid | 0.5 | 2.0 | 2.0 | 3.3 | 1.0 |
| Disodium Phenyl Dibenzimidazole Tetrasulfonate | 1.0 | 1.0 | 1.5 | 2.3 | 0.5 |
| Extract A | 0.2 | | 0.35 | | |
| Extract B | | 1.1 | | | |
| Extract C | | | | 0.8 | 0.7 |
| Biotin | | 0.02 | | | |
| Retinyl Palmitate | | | | 0.2 | |
| Tocopheryl Acetate | | 1.0 | | | 0.5 |
| Ascorbic Acid | | | 0.05 | | |
| Trisodium EDTA | | | 0.2 | 0.1 | |
| Phenoxyethanol | 0.5 | 0.4 | 0.5 | | 0.3 |
| Butylparaben | 0.1 | | | 0.4 | 0.6 |
| Ethylhexylglycerin | 0.2 | 0.2 | 0.1 | 0.4 | |
| Alcohol Denat. | | 8.0 | | | 3.0 |
| Xanthan Gum | | 0.1 | | | |
| Gellan Gum | 0.2 | | 0.1 | | 0.1 |
| Carbomer | | 0.2 | | | |
| Glycerin | 10 | 5.0 | 6.0 | 4.0 | 7.0 |
| Butylene Glycol | | | | 2.0 | |
| Additives (distarch phosphate, $SiO_2$, talc, BHT, aluminum stearate) | 0.03 | | 0.05 | 3.0 | |
| Parfum | q.s. | q.s. | q.s. | q.s. | q.s. |
| Aqua | ad 100 | ad 100 | ad 100 | ad 100 | ad 100 |

| Example number | 11 | 12 | 13 | 14 | 15 |
|---|---|---|---|---|---|
| PEG-100 Stearate | 1.4 | 0.1 | | 1.2 | |
| Glyceryl Stearate | 1.4 | 0.5 | 0.2 | 1.0 | 0.9 |
| Ceteareth-100 | | 2 | 3.1 | | 2.1 |
| Sorbitan Stearate | 2.3 | | | 2.5 | |
| Polysorbate 60 | 0.1 | | 0.3 | 0.8 | 0.7 |
| Polysorbate 80 | 0.8 | 0.5 | | | 0.1 |
| Sorbitan Isostearate | 0.1 | 0.25 | | 0.05 | |
| *Theobroma Grandiflorum* Seed Butter | 3.0 | | | 1.2 | 2.7 |
| *Butyrospermum Parkii* (Shea) Butter | | 2.5 | 3.5 | 1.9 | |
| Jojoba Esters | 2.0 | 2.5 | 1.3 | 0.5 | 1.0 |
| Beeswax | 1.0 | 0.2 | 0.8 | 1.6 | 2.0 |
| *Helianthus Annuus* Seed Oil | 0.5 | | | 0.1 | |
| *Persea Gratissima* Oil | | 0.7 | | 0.3 | 0.5 |
| *Olea Europaea* Fruit Oil | | 0.1 | 0.6 | 0.1 | |
| Cyclomethicone | | 3.6 | 0.1 | 0.1 | 1.2 |
| Dimethicone | 5.4 | | 4.5 | 5.0 | 3.6 |
| Squalane | 3.0 | | | | 1.9 |
| Carbomer | | 0.2 | 0.4 | | 0.15 |
| Hydroxyethyl Acrylate/Sodium Acryloyldimethyl Taurate Copolymer | 1.7 | 0.1 | 1.0 | 2.0 | 0.1 |
| Polymethyl Methacrylate | 0.5 | 0.6 | 0.1 | | |
| Dimethicone Crosspolymer | 0.6 | 0.3 | | 0.25 | |
| Pullulan | 0.5 | | 0.4 | | |
| Carrageenan | 0.2 | 0.3 | | 0.7 | 0.3 |
| Caprylyl Glycol | 0.3 | | 0.1 | 0.25 | |

-continued

| Example number | 11 | 12 | 13 | 14 | 15 |
|---|---|---|---|---|---|
| Methylpropanediol | | 1.3 | | | |
| Glycerin | 3.1 | 1.7 | 4.0 | 2.8 | 3.5 |
| Sorbitol | | | | 0.1 | |
| Propanediol | 2.0 | | 1.9 | | |
| Propylene Glycol | 0.1 | | 0.1 | 0.2 | 0.3 |
| Pentylene Glycol | 0.1 | 0.5 | | | |
| Butylene Glycol | 0.2 | | 0.3 | 0.2 | |
| Tocopherol Acetate | 0.5 | 0.2 | | 0.45 | 0.35 |
| Ubiquinone | | 0.1 | 0.2 | | 0.15 |
| Retinyl Palmitate | | 0.15 | | 0.15 | |
| Extract A | | | 0.65 | | 0.01 |
| Extract B | | 0.7 | | | |
| Extract C | 0.25 | | | 0.35 | |
| Disodium EDTA | 0.1 | 0.1 | 0.1 | 0.1 | 0.1 |
| Triethanolamine | 0.1 | 0.1 | 0.1 | 0.1 | 0.1 |
| Phenoxyethanol | 0.4 | 0.3 | 0.5 | 0.3 | 0.45 |
| Ethylhexylglycerin | | 0.2 | | 0.1 | 0.05 |
| Titanium Dioxide | 0.3 | 0.1 | | | 0.2 |
| Tapioca Starch | | | 0.05 | | |
| Talc | | 0.05 | | | |
| Parfum | q.s. | q.s. | q.s. | q.s. | q.s. |
| Aqua | ad 100 | ad 100 | ad 100 | ad 100 | ad 100 |

What is claimed is:

1. A method for the expression and/or for the amplification of the expression of thrombospondin-1, fibronectin, vimentin and/or mimecan in human skin, wherein the method comprises applying to human skin at least one caviar extract in an amount which is capable of causing at least one of the expression and the amplification of the expression of at least one of thrombospondin-1, fibronectin, vimentin, and mimecan in human skin.

2. The method of claim 1, wherein a cosmetic preparation comprising the at least one caviar extract is applied to the human skin.

3. The method of claim 1, wherein at least one of thrombospondin-1, fibronectin, vimentin and/or mimecan is caused to be expressed in human skin.

4. The method of claim 1, wherein the at least one caviar extract has been obtained from fish eggs of white sturgeon (Acipenser transmontanus) and/or of Siberian sturgeon (Acipenser baerii).

5. The method of claim 1, wherein the at least one caviar extract has been obtained by a process comprising (1) homogenizing provided fish eggs in at least one solvent, (2) extracting at least one liquid phase from the homogenizate obtained in (1), and (3) optionally filtering the extract obtained in (2).

6. The method of claim 5, wherein at least one caviar extract is used, in a preparation of which at least water, but no glycol, or glycol in ratios by weight of water to glycol of from 1.1:1.0 to 1000:1.0, is added as solvent during the homogenization of the fish eggs and in which an aqueous phase of the homogenizate is extracted to obtain the at least one caviar extract.

7. The method of claim 5, wherein at least one caviar extract is used, in the preparation of which at least glycol and optionally water are added as solvent during the homogenization of the fish eggs, where a ratio by weight of water to glycol is from 1.0:1.0 to 1.0:1000, and in which a glycolic phase of the homogenizate is extracted to obtain the at least one caviar extract.

8. The method of claim 5, wherein at least one caviar extract is used, in the preparation of which at least one oil is added as solvent during the homogenization of the fish eggs and in which an oil phase is extracted.

9. The method of claim 8, wherein, as oil, triglycerides are used.

10. The method of claim 8, wherein a ratio by weight of the fish eggs to the added oil phase during the homogenization is from 1.0:0.1 to 1.0:1.0.

11. The method of claim 6, wherein a ratio by weight of the fish eggs to aqueous phase, when present, is from 1.0:10 to 1.0:1.0.

12. The method of claim 7, wherein a ratio by weight of the fish eggs to aqueous phase, when present, is from 1.0:10 to 1.0:1.0.

13. The method of claim 1, wherein mannose phosphate is additionally employed.

14. The method of claim 1, wherein mannose is additionally employed.

15. The method of claim 1, wherein at least two different caviar extracts are employed.

16. The method of claim 1, wherein at least three different caviar extracts are employed.

17. The method of claim 16, wherein there are employed a first lipophilic caviar extract, in the preparation of which at least one oil is added as solvent during a homogenization of the fish eggs and in which an oil phase is extracted to obtain a lipophilic caviar extract, a second aqueous caviar extract, in the preparation of which at least water, but no glycol, is added as solvent during a homogenization of the fish eggs and in which an aqueous phase is extracted to obtain the aqueous caviar extract, and a third glycolic caviar extract, in the preparation of which at least glycol is added as solvent during a homogenization of the fish eggs and in which a glycolic phase is extracted to obtain the third caviar extract.

18. A method of reinforcing at least one of the skin ligaments, the retinacula cutis, and the connective tissue strands in human skin, wherein the method comprises applying at least one caviar extract in an amount which is capable of reinforcing at least one of the skin ligaments, the retinacula cutis, and the connective tissue strands in human skin to human skin.

19. The method of claim 1, wherein sodium mannose phosphate is additionally employed.

20. The method of claim 1, wherein the at least one caviar extract is capable of causing at least one of the expression and the amplification of the expression of at least one of thrombospondin-1, vimentin, and mimecan in human skin.

* * * * *